(12) United States Patent
Bergman

(10) Patent No.: US 6,339,177 B1
(45) Date of Patent: Jan. 15, 2002

(54) DINITROALKYL AROMATICS POLYMERIZATION RETARDERS OR INHIBITORS AND METHODS FOR MAKING AND FOR USING SAME

(75) Inventor: Lee H. Bergman, Houston, TX (US)

(73) Assignee: Sea Lion Technology, Inc., Texas City, TX (US)

(*) Notice: Subject to any disclaimer, the term of this patent is extended or adjusted under 35 U.S.C. 154(b) by 0 days.

(21) Appl. No.: 09/577,632

(22) Filed: May 24, 2000

(51) Int. Cl.[7] ................... C07C 205/06; C09K 3/00
(52) U.S. Cl. ................... 568/711; 252/182.29
(58) Field of Search ................ 252/182.29; 568/711

(56) References Cited

U.S. PATENT DOCUMENTS

| | | | | |
|---|---|---|---|---|
| 2,810,767 A | * | 10/1957 | Clarke et al. ............... | 562/73 |
| 3,766,276 A | * | 10/1973 | Goddard ................ | 260/624 R |
| 3,932,537 A | | 1/1976 | Wetzel et al. ........... | 260/624 C |
| 4,055,605 A | | 10/1977 | Jarreau, Sr. ............ | 260/624 R |
| 4,092,367 A | | 5/1978 | Bridwell et al. .......... | 568/785 |
| 4,198,531 A | | 4/1980 | Merger et al. ............. | 568/793 |
| 4,236,033 A | | 11/1980 | Alfs et al. ............... | 568/793 |
| 4,391,998 A | | 7/1983 | Wu ...................... | 568/781 |
| 4,418,222 A | | 11/1983 | Honnen .................. | 568/793 |
| 4,599,465 A | | 7/1986 | Tamaru et al. ............ | 568/781 |
| 4,664,845 A | * | 5/1987 | Jancis et al. ............. | 203/9 |
| RE33,168 E | | 2/1990 | McDaniel ................ | 564/411 |
| 5,171,896 A | | 12/1992 | Knifton et al. ........... | 568/791 |
| 5,254,760 A | | 10/1993 | Winter et al. ............ | 585/5 |
| 5,276,215 A | | 1/1994 | Knifton et al. ........... | 568/794 |
| 5,300,703 A | | 4/1994 | Knifton et al. ........... | 568/794 |
| 5,446,220 A | * | 8/1995 | Arhancet ................ | 585/3 |

FOREIGN PATENT DOCUMENTS

GB          1 294 781          11/1972          ........... C07C/37/12

OTHER PUBLICATIONS

"Alkylation of Phenols" in Kirkothmer Encyclopedia of Chemical Technology Third Edition, vol. 2, pp. 65–66. Interscience Publishers, A Division of John wiley and Compnany, N.Y. (1978).

* cited by examiner

Primary Examiner—Sreeni Padmanabhan
Assistant Examiner—Brian J. Davis
(74) Attorney, Agent, or Firm—Robert W. Strozier

(57) ABSTRACT

A vinyl monomer inhibitor systems is disclosed which includes 2,6-dinitro-4-alkylated phenols and mixtures of 2,6-dinitro-4-alkylated phenols and 2,4-dinitro-6-alkylated phenols as well as vinyl monomer stabilized composition including an effective amount of the inhibitor systems. A method for the preparation and use is also disclosed where phenol is first alkylated under conditions that afford predominately monoalkylated phenols having a high para alkylation preference, followed by nitration of the alkylated phenols to form a dinitrated, monoalkylated product.

20 Claims, 1 Drawing Sheet

DINITROALKYL AROMATICS POLYMERIZATION RETARDERS OR INHIBITORS AND METHODS FOR MAKING AND FOR USING SAME

BACKGROUND OF THE INVENTION

1. Field of the Invention

The present invention relates to dinitroalkylphenols, methods for making the dinitroalkylphenols and methods for using the dinitroalkylphenols as polymerization inhibitors.

More particularly, the present invention relates to compositions comprising 2,6-dinitro-4-alkylphenols and mixtures of 2,6-dinitro-4-alkylphenols and 2,4-dinitro-6-alkylphenols where the mixture comprises the natural isomer mix derived during phenol alkylation, polymerization inhibitors composed of 2,6-dinitro-4-alkylphenols and mixtures of 2,6-dinitro-4-alkylphenols and 2,4-dinitro-6-alkylphenols, methods for making and using same.

2. Description of the Related Art

Alkylated dinitro phenols or hydroxy aromatics are used to inhibit olefin polymerization by deactivating radicals that lead to polymerization. Generally, when phenolic compounds are alkylated, the resulting product mixture does not contain a single product. For example, in the manufacture of 2-alkylphenol, the manufacturing process requires some type of separation step to remove undesired by-products, namely 4-alkylphenol, prior to selling a substantially pure 2-alkylphenol as an inhibitor.

Thus, there is a need in the art for more cost effective polymerization inhibitors and more cost effective methods for preparing inhibitors, where alkylation and nitration can be performed without concern for product separation or purification, including the separation of monoalkylated phenols.

SUMMARY OF THE INVENTION

The present invention addresses these needs by providing dinitroalkylphenolic polymerization inhibitors of formula (I):

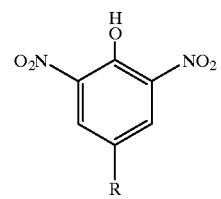

where R is an alkyl group having between about 3 and 12 carbon atoms, preferably 3 to 6 carbon atoms.

The present invention also provides a vinyl polymerization inhibitor comprising a mixture of dinitroalkylphenolic polymerization inhibitors of formulas (I) and (II):

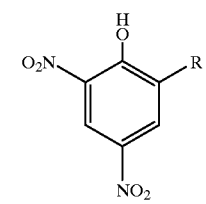

where R is an alkyl group having between about 3 and 12 carbon atoms, preferably 3 to 6 carbon atoms.

The present invention provides a method for making a mixture of inhibitors of formulas (I) and (II) including the steps of alkylating phenol with an olefin having between about 3 and about 12 carbon atoms under conditions sufficient to promote the alkylation and form an alkylated phenol composition comprising mono-alkylated phenols and minor amount of di and tri alkylated phenols. The unwanted formation of di and tri alkylated phenols can be minimized by controlling the extent of phenol conversion, i.e., allowing only partial phenol conversion coupled with phenol recycle. The alkylated phenol composition is then nitrated under conditions sufficient to form a nitrated phenol composition comprising dinitrated mono-alkylated phenols and minor amount of mononitrated dialkylphenols and other nitrated species. The resulting nitrated composition comprises predominantly 2,4-dinitro-6-alkylphenol and 2,6-dinitro-4-alkylphenol. Alternatively, the method can also include the step of separating the monoalkylated phenols from any di or tri alkylated phenols prior to nitration, unless the di and tri alkylated phenols comprises less than about 5 wt. % of the entire composition.

The present invention also provides a vinyl monomer stabilized composition comprising a vinyl monomer and an inhibitor system of the present invention and to a method for inhibiting vinyl monomer polymerization including the step of adding an effective inhibiting amount of an inhibitor comprising a mixture of dinitroalkylphenolic polymerization inhibitors of formulas (I) and (II).

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
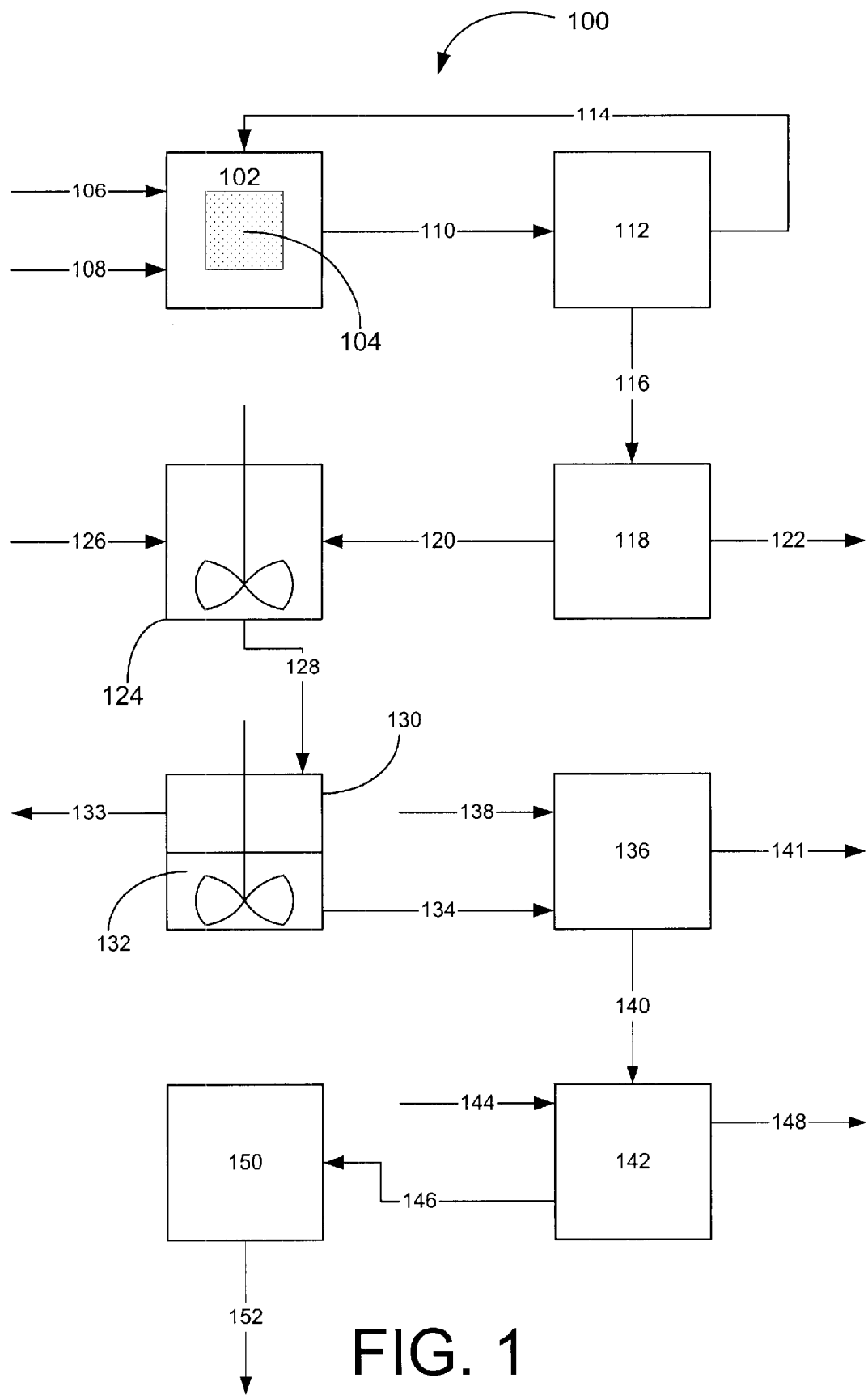
FIG. 1 depicts one overall process scheme of the present invention.

The inventor has found that a lower cost polymerization inhibitor can be prepared by alkylating phenol with an alkene having between about 3 and about 12 carbon atoms to form an alkylated phenol reaction product including mainly monoalkylated phenols and minor amount of di and tri alkylated phenols. The inventor has also found that the amount of di and tri alkylated phenols formed in the alkylation step can be minimized by controlling the conversion of phenol coupled with recycling phenol. The alkylated phenol reaction product is then nitrated to produce a composition including predominantly dinitro-monoalkylated phenols. The inventor has also found that 2,6-dinitro-4-alkyl phenols inhibit or prevent vinyl monomer polymerization as effectively or more effectively than their 2,4-dinitro6-alkyl phenol analogs and that mixtures of the two are also effective inhibitors. The ability to use a mixture of the two dinitro-monoalkylated phenols provides substantial cost saving eliminating a difficult product separation step required to purify the nitration feedstock (the monoalkylated phenols) so that a substantially pure dinitro-monoalkyl phenol inhibitor can be produced. Moreover, mixtures of ortho and para isomers of dinitro-monoalkylated phenols have lower freezing point than either isomer. As an example a 50-50 mixture of 2,4-dinitro-6-sec-butyl phenol and 2,6-dinitro-4-sec-butyl phenol has a freezing point about 20° C. lower than the freezing point of the pure isomers.

The present invention broadly relates of vinyl polymerization inhibitors including at least one compound of formula (I):

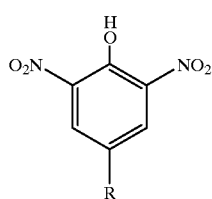

(I)

alone or in a combination with at least one compound of formula (II)

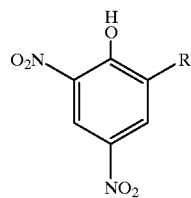

(II)

where R is an alkyl group having between about 3 and 12 carbon atoms, preferably 3 to 6 carbon atoms.

The present invention also broadly relates to a method for preparing a vinyl polymerization inhibitor comprising a mixture of at least one compound of formula (I) and at least one compound of formula (II). The method includes the step of alkylating phenol with an olefin having between about 3 and about 12 carbon atoms to from an alkylated phenol reaction product comprising primarily 2-alkylphenol, 4-alkylphenol and dialkylated phenols. After the phenol is stripped and optionally di and tri alkylated phenols are separated from the monoalkylated phenols, the alkylated phenol intermediate product is nitrated under conditions sufficient to prompt dinitration of mono-alkylated phenol components of the reaction product to form an inhibitor mixture comprising compounds of formulas (I) and (II) and dinitrated dialkylated phenols.

The present invention further broadly relates to a method for inhibiting vinyl monomer polymerization including adding an effective amount of an inhibitor mixture comprising at least one compound of formula (I) and at least one compound of formula (II).

The inhibitor mixtures of the present invention are designed to inhibit or slow the vinyl monomer polymerization during certain vinyl monomer processes such as distillation, other elevated temperature processing of vinyl monomer streams, or the like. Generally, the mixture is simply added to the vinyl monomers as a neat material or in a suitable solvent provided, however, that the inhibitor mixtures of the present invention have sufficient solubility in the given solvent.

For continuous processes that involve vinyl monomers either during production, purification and/or transformation, an inhibitor composition of the present invention is generally metered into the reaction vessel containing the vinyl monomers for which polymerization inhibition is desired. The amount metered into the process will depend on processing conditions such as time, temperature, pressure, light, air/oxygen or other conditions and will generally be the minimum amount needed to prevent or slow polymerization over a given period of time.

The present invention also relates to stabilized vinyl aromatic composition comprising a vinyl aromatic monomer and a polymerization inhibitorily effective amount of an inhibitor composition of the present invention. The stabilized vinyl aromatic composition of this invention may be in the form of a reaction mixture additionally comprising the starting materials of the vinyl aromatic compound to be stabilized as well as by-products of the production process. Thus, in the case of styrene, the product from the dehydrogenation of ethylbenzene would typically include styrene, ethyl benzene and by-products.

The inhibitor systems of this invention are especially suited to prevent or slow vinyl aromatic compound polymerization during formation and/or purification via distillation or the like. A preferred use of the inhibitor or retarder compositions of this invention is the formation and purification of styrene. Styrene is generally formed by the dehydrogenation of ethylbenzene. As styrene is formed, the possibility of styrene polymerization ensues. To prevent, slow or retard styrene polymerization, retarders such as the retarders of the present invention are added to the reaction streams on a continuous bases at a level sufficient to reduce polymer formation and keep polymer formation below a given amount. The retarders of this invention are used during the entire styrene formation and purification process including the steps needed to remove the starting material ethylbenzene and lower boiling by-products. Typically, this involves the sequential distillation of the reaction product through a plurality of distillation columns. In the first of such columns, a relatively large amount of starting material and by-products will be present, while in the last column essentially pure styrene (plus polymerization inhibitors and heavy, nondistillable byproducts) will be present.

The inhibitor compositions of the present invention are also useful for the vacuum distillation of various readily polymerizable vinyl aromatic compounds such as styrene, α-methyl styrene, vinyl toluene, divinylbenzene, or the like.

Besides styrene, the inhibitors of this invention are also well suited for use with divinylbenzene and other vinyl aromatics as well. Divinylbenzene is generally produced commercially by a catalytic dehydrogenation of a mixture of the isomers of diethylbenzene. Such mixtures of diethylbenzene isomers are usually produced as a by-product of a process for making ethylbenzene by the Friedel-Crafts ethylation of benzene. Products obtained from dehydrogenation of diethylbenzenes generally contain a mixture of divinylbenzenes, ethylvinylbenzenes, unreacted diethylbenzenes, a small quantity of naphthylene, and some impurities. Thus, a typical feed stream for the divinylbenzene distillation system comprises low boiling materials (such as styrene and ethylbenzene), diethylbenzene, ethylvinylbenzene and divinylbenzene.

The polymerization inhibitor system of this invention will provide stability against vinyl aromatic polymerization at temperatures typically employed for the purification of vinyl aromatic compounds (i.e., from about 90° C. to about 140° C.) for periods well in excess of those typically employed for such purification.

The methods of this invention comprise the addition to a vinyl aromatic composition of an effective amount of the instant polymerization inhibitor system. As employed herein, the term "effective amount" generally refers to that amount of inhibitor which is needed to prevent the formation of between about 0.1 weight percent (wt. %) to about 5 wt % of vinyl aromatic polymer during distillation at temperatures of between about 90° C. and about 140° C. or during other vinyl monomer processing, where the lower polymer amounts are generally for styrene monomers and the higher polymer amount are generally for DVB or the like. However, an effective amount can be adjusted to ensure that no more than a desired amount of polymer is formed in a given transformation such as distillation or the like.

The amount of the polymerization inhibitor used in the present invention to inhibit the polymerization of vinyl aromatic compounds may vary over a broad range depending upon many factors including the identity of the compound to be distilled, the feed stream composition, the degree of inhibition desired, the distillation conditions such as the temperature, pressure, reflux ratio, residence time, design of the distillation apparatus etc. Needless to say, different vinyl aromatic compounds have different tendencies for thermal polymerization, and generally speaking the larger the amount of inhibitor used the larger is the effect of inhibition of polymerization. Excessive amounts of inhibitor should be avoided, however, for various reasons such as increased cost of the inhibitor and increased risk of contamination of the distilled product.

In general, such an effective amount will depend on the vinyl aromatic compound used and on the exact physical conditions of the processing. Generally, for use in styrene processing, an effective amount of the inhibitors of this inventions is between about 1 part per million (ppm) and about 3,000 ppm by weight based on the weight of styrene. Preferably, an effective amount is between about 100 ppm and about 1,500 ppm by weight of styrene. Particularly, an effective amount is between about 500 ppm and about 1,500 ppm by weight of styrene. In the case of divinylbenzene (DVB), an effective amount will generally be between about 100 ppm and about 50,000 ppm by weight based on the weight of DVB, preferably between about 500 ppm and about 30,000 ppm and particularly, between about 2,000 ppm and about 20,000 ppm.

If a retarder system of the present invention is used in conjunction with or in addition to a "true" inhibitor system, then an effective amount of the inhibitor system of the present invention will be less than an effective amount used in the absence of the true inhibitor system. When using a combination of a true inhibitor composition and a retarder composition of this invention, the amount of each compound in the combination will depend on cost and performance. Thus, the amount of a compound of Formulas I or II and the amount of true inhibitor can be adjusted to give any desired protection at any desired cost. True inhibitors are generally about 10 times more expensive than the retarders of the present invention. True inhibitors include, without limitation, nitroxides, hydroxylamines, N-nitrosoamines or the like.

Although this invention is preferably directed to mononuclear hydroxylated aromatics, the invention can utilize phenolic compounds in general. Thus, "phenol" or "phenolic compounds" includes, depending on the context, for example, substituted phenols, hydroxy naphthylenes, or the like. Thus, the aromatic group of a "phenol" can be mononuclear or polynuclear, substituted, and can include other types of aromatic groups as well.

Alkylation

The attachment of a hydrocarbyl group to phenol or to a phenolic compound in general can be accomplished by a number of techniques well-known to those skilled in the art. One particularly suitable technique is the Friedel-Crafts alkylation reaction, wherein an olefin is reacted with a phenol in the presence of a Lewis acid catalyst. Methods and conditions for carrying out such reactions are well-known to those skilled in the art. See, e.g., the discussion in the article entitled, "Alkylation of Phenols" in "KirkOthmer Encyclopedia of Chemical Technology", Third Edition, Vol. 2, pages 65–66, Interscience Publishers, a division of John Wiley and Company, N.Y. Other equally appropriate and convenient techniques for attaching a hydrocarbyl group to phenol or other phenolic starting material will occur readily to those skilled in the art.

Specific illustrative examples of hydrocarbyl-substituted hydroxyaromatic compounds include hydrocarbyl substituted-phenol, naphthol, 2,2'-dihydroxybiphenyl, 4,4-dihydroxybiphenyl, 3-hydroxyanthracene, 1,2,10-anthracenetriol, and resorcinol; octyl phenol, propylene tetramer-substituted phenol, propylene oligomer ($M_n$ 300–800)-substituted phenol, polybutene ($M_n$ about 1000) substituted phenol, substituted naphthols corresponding to the above exemplified phenols, methylene-bis-phenol, bis-(4-hydroxyphenyl)-2,2-propane, and hydrocarbon substituted bis-phenols, for example, octyl, dodecyl, oleyl, polybutenyl, etc., sulfide-and polysulfide-linked analogues of any of the above, alkoxylated derivatives of any of the above hydroxy aromatic compounds, etc. n "Bisphenol A and Alkylated Phenols", SRI PEP Report No. 192 (December 1988).

The alkylation reaction generally takes place at or near atmospheric pressure in the presence of an acidic catalyst such as a mineral acid, a Lewis acid (e.g. boron trifluoride) or a cation exchange resin (e.g. styrene-divinyl benzene resin). The acid catalysts lead to predominantly para-alkylated phenol when the para position is available. Generally a molar ratio of phenol to olefin of about 1.5 to about 3:1 is desired to minimize the yield of dialkylphenols.

The process for continuous manufacture of alkylphenols by reacting phenol with olefin at between about 70° C. and about 140° C. in a fixed bed of an organic sulfonic acid cation exchange resin as disclosed in U.S. Pat. No. 4,198,531, incorporated herein by reference can be used in the present invention. As well as other alkylation processes such as those disclosed in U.S. Pat. Nos. RE 33,168, 5,300,703, 5,276,215, 5,171,896, 4,599,465, 4,418,222, 4,391,998, 4,236,033, 4,198,531, 4,092,367, 4,055,605, 3,932,537 and 3,766,276, incorporated herein by reference.

Illustrative examples of alkylphenols include, without limitation, o and p-tert-butylphenol, o and p-isopropylphenol, o and p-sec-butylphenol, o and p-tert-octylphenol, o and p-nonylphenol, o and p-dodecylphenol or the like.

The alkylation of phenol according to this invention results in a reaction product composed of from about 5 wt % to about 95 wt % of the ortho isomer and about 95 wt % to about 5 wt % of the para isomer. For example, compositions can be a 50/50 mixture of the ortho and para isomers; 60/40 mixtures of the two isomers with either being the predominated isomer; 70/30 mixture; 80/20 mixture; 90/10 mixture; and mixtures with greater than 90 wt % of one isomer and the remainder being the other isomer. It should be recognized that the above isomer ratios relate the amount of dinitro-monoalkylphenol present in the composition. Thus, the ratios are generally corrected to ignore by-product concentration such as nitrated dialkyl phenols and trialkylphenols. Such by-products generally make up less than about 5 wt % of the entire composition, and preferably less than less than 3 wt % the entire composition.

Nitration

The present invention also relates to the dinitration of alkylkated phenols. Nitration is also a well-known process generally employing relatively dilute and then more concentrated nitric acid as the nitrating agent. The nitration reaction can be performed in a single stage where the monoalkylated phenols are first mono-nitrated and then dinitrated in the same reactor or in two stages where nitration occur sequentially and the mononitration step uses spent nitric acid from the second or dinitration step. Preferably, the mono-alkyl phenols are first reacted with sulfuric acid to from a intermediate sulfated product which is then reacted with nitric acid to form the dinitro-monoalkylphenyls.

DETAILED DESCRIPTION OF THE DRAWINGS

Now referring to FIG. 1, one preferred overall reaction scheme generally 100 is shown to include an alkylation reactor 102 having an ion exchange resin catalyst 104 therein into which is fed a hydroxy aromatic stream 106 and an alkene stream 108 to form an intermediate stream 110. The alkylation reaction is generally carried out at a temperature of about 100° C. The stream 110 is forwarded to a flash unit 112 where unreacted phenol, alkenes and lights 114 are flashed from the intermediate stream 110 to form an intermediate bottom stream 116. Preferably, stream 114 is recycled to the alkylation reactor 102. The stream 116 is then forwarded to a distillation or fractionation column 118 where the stream 116 is fractionated into a monoalkylation stream 120 and a heavies stream 122. The monoalkylation stream 120 comprises substantially 2 and 4 alkylphenol with minor amount of heavy by-products where the amount of heavy by products (di and tri alkylphenols) is a function of the number of theoretical separation stages in the column or is separation efficiency.

The monoalkylation stream 120 is then forwarded to a stirring tank 134 in which a molar excess of sulfuric acid is added an a sulfuric acid stream 126. Streams 126 and 120 are mixed to form a sulfonated aromatic stream 128. The sulfonated aromatic stream 128 is then forwarded to a nitration reactor 130 containing nitric acid 132. The nitration reactor 130 supports a two phase reaction and uses a 20% nitric acid solution as the nitrating agent. The nitration reaction is generally carried out at a temperature between about 60° C. and about 75° C. The pre-reaction with sulfuric acid increases the efficiency and lower the processing costs associated with the nitration.

After the nitration reaction is completed, a top phase waste acid stream 133 and a bottom phase crude product stream 134 are removed from the reactor 130 and the crude product stream 134 is forwarded to a base wash unit 136 where a diluted sodium bicarbonate wash stream 138 is added to form a neutralized product stream 140 and a waste neutralized acid stream 141. Although dilute sodium bicarbonate is used in the neutralization step other bases can be used provided that the base is not strong enough to emulsify the reaction product. The neutralized product stream 140 is then forwarded to a water wash unit 142 where a water stream 144 is added to form a washed product stream 146 and a waste water stream 148. The washed product stream 146 is then dewatered in a flast unit 150 to form a final product stream 152, where the residual water is removed under vacuum at a temperature range between about 60° C. and about 80° C. The water wash is generally carried out at a temperatures of about 50° C. The dewatering step is under vacuum sufficient to reduce the water concentration to at least 1000 ppm by weight. The final product generally includes less than 0.05 wt % sulfuric acid.

The reactor 102 can be any standard reactor known in the art such as a stirred tank reactor, a column reactor, a counter-flow reactor or any other reactor typically used to alkylate aromatic compounds. The flash units can be any standard flash unit known in the art such as a traditional distillation column. Preferably, the flash unit is a distillation unit with short residence time, low pressure and low temperature to reduce further conversion to di and tri alkylphenols such as a packed column or use of a falling film reboiler or other similar low pressure, low temperature separation apparatus. The neutralization tank is any tank known in the art including a simple stirred tank. The separator is any separator for separating an organic phase from an aqueous phase known in the art such as a decanting unit (organics taken off the top and the aqueous phase taken from the bottom). The mixing units can be any mixing unit known in the art such as a simple stirred tank.

Although an ion exchange resin was used as the alkylation catalyst, any other alkylation catalyst can be used as well such as boron trifluoride, phosphoric acid, sulfuric acid or the like. Moreover, acid modified ion exchanger resins can also be used, but the ortho to para mix is generally different than for simple strong acids. The amount of sulfuric acid added to the alkylated intermediates prior in the stirring tank is preferably 1 to 1 mole based. It is thought that a sulfate ester of the alkylated hydroxy compound forms which promotes nitration by nitric acid. The nitric acid is generally 20 wt % solution in water with a 2 to 3 molar excess of nitric acid to alkylated phenolics. The nitration reaction is generally performed in the absence of oxygen to reduce unwanted peroxide formation.

The nitrated reaction product is then washed. The wash step can be simply water or a weak base wash using dilute carbonate, bicarbonate or a mixture thereof. Solvents such as hexane and octane that have boiling points close to phenol or the hydroxy aromatic compound improve strip efficiencies and help to reduce the concentration of mono-alkylated product thereby reducing di and tri alkylated by-products. Generally, the crude alkylation product includes less than 1 wt % di/tri alkylated by-products, less then 0.1 wt % residual unreacted hydroxy aromatic compound and less than 0.3 wt % meta alkylated product. The overall yield is generally between at least 85%, preferably at least 90%, and particularly at least 95%. The product is generally at least 70 wt % of the para isomer or a compound of formula (I), preferably, at least 80 wt % of the para isomer, particularly, at least 90 wt % of the para isomer and especially, at least 95 wt % of the para isomer.

Suitable vinyl monomers for which the inhibitor mixtures of the present invention are intended include, without limitation, olefins such as 1-alkenes and internal alkenes, acrylics, vinyl acetate, vinyl aromatic compounds, vinyl naphthylenes, vinyl pyridine, or the like, dienes including conjugated and non-conjugated dienes, or any other monomer including a vinyl group. Illustrative non-limiting examples of the vinyl aromatic compounds which may be stabilized against polymerization by the process of this invention are styrene, alpha-methylstyrene, vinyltoluene and divinylbenzene, as well as halogenated species thereof.

The polymerization inhibitor compositions of this invention may further comprise an aromatic hydrocarbon solvent. Suitable solvent include, without limitation, benzene, toluene, xylene, ethylbenzene and other alkyl-benzenes as well as vinyl aromatic compounds themselves such as styrene, alpha-methylstyrene and the like. Typically, when solvents are employed the hydrogenated precursors of the vinyl aromatic to be stabilized are the preferred solvents. Thus, for the stabilization of styrene, ethyl benzene or styrene are the preferred solvent. Similarly for the stabilization of alpha-methylstyrene, isopropylbenzene is the preferred solvent.

Preferably, no solvent is used in the alkylation step. However, the alkylation can be run in the presence of solvents that can be easily separated from the starting compounds and the desired products.

Preferably no solvent is used in the nitration step. However, the nitration step can be run in the presence of solvents such as acetic acid or chlorinated solvent such as chloroform.

Suitable olefins for use in the alkylation step of the present invention include, without limitation, 1-alkene and 2-alkene having between 3 and 12 carbon atoms such as propene, 1-butene, 2-butene, 2-methyl-1-propene, 1-pentene, 2-pentene, 3-methyl-1-butene, 1-hexene, 2-hexene, 3-hexene, 4-methyl-1-pentene, 4-methyl-2-pentene, or the like.

EXAMPLES

The following examples illustrate the preparation and use of the inhibitors and inhibitor mixtures of the present invention and should not be construed to limit the scope or content of this application which is amenable to modifications and improvements to those of ordinary skill in the art.

Example 1

This example illustrates the nitration of alkylated phenol starting materials to form retarder composition of this invention comprising a mixture of at least one compound of formula (I) and at least one compound of formula (II).

Sample A is a commercial sample of 2-butylphenol having the following specs: 98.6 wt % 2-butylphenol, 1.3 wt % 4- butylphenol and <0.1 wt % 2,4/2,6-di-butylphenol. Sample B is a commercial sample of 4- butylphenol having the following specs: 98.2 wt % 4-butylphenol, 0.9 wt % 2-butylphenol and 0.2 wt % 2,4/2,6-di-butylphenol. Sample C is a laboratory prepared starting material having the following specs: 79.5 wt % 2-butylphenol, 15.1 wt % 4-butylphenol and 4.3 wt % 2,4/2,6-di-butylphenol. Sample C was prepared by alkylating phenol with 1-butene at 100° C. over an ion exchange resin catalyst (Rohm & Haas Amberlyst 36 (dry)). Unreacted phenol was stripped from the alkylation product and the product was fractionated to remove high boiling impurities.

A given amount of Samples A, B or C was premixed with 1.67 moles of 98% sulfuric acid per mole of butylphenol. The premix was then added to a stirred solution of 19% nitric acid containing 3.5 moles of nitric acid per mole of butylphenol. The addition took place over one hour at a temperature of about 60° C. The reaction mixture was held at 60° C. for ½ hours. The temperature was then raised to 70° C. and held for an additional hour. The product layer, the bottom layer, was separated from the upper aqueous acid layer. The resulting product was then washed with water at 70° C. to remove residual acid and dried under vacuum.

Example 2

This example illustrates the styrene polymerization inhibiting properties of nitrated Samples A, B and C.

Styrene was pretreated to remove TBC (tert.-butylcatechol), a storage inhibitor. 500 ppm by weight of each nitrated sample A, B or C was added to quantity of styrene and the mixture was sealed in a 3 cc glass ampule and purged with nitrogen. The ampules were immersed in a 120° C. oil bath and aliquots from each ampule were withdrawn at specified times after immersion. Each aliquot was rapidly cooled to below 20° C. in an ice bath and the polymer content was measured. The results are shown in Table I.

TABLE I

| | Styrene Polymerization Inhibition Data | | |
|---|---|---|---|
| Hours | A | B | C |
| 0.00 | 0.00 | 0.00 | 0.00 |
| 0.25 | 0.03 | 0.02 | 0.02 |
| 0.5 | 0.13 | 0.12 | 0.12 |
| 1.0 | 0.41 | 0.35 | 0.35 |
| 1.5 | 0.44 | 0.44 | 0.44 |
| 2.0 | 0.49 | 0.42 | 0.48 |
| 3.0 | 0.81 | 0.89 | 0.84 |
| 4.0 | 1.55 | 1.47 | 1.64 |

The results show that within experimental error, the three retarders showed equal inhibition of styrene polymerization.

Example 3

This example illustrates the polymerization inhibiting properties of an inhibiting mixture of 2,4-dinitro-4-sec-butyl phenol and 2,6-dinitro-4-sec-butyl phenol.

To a solution of styrene is added an amount of 2,4-dinitro-4-sec-butyl phenol (24DNBP) to yield a final concentration of 500 ppm. The temperature is then raised to 120° C. and maintained during the course of the study. At 0.5, 1.0, 1.5, 2.0, 3.0 and 4.0 hours samples are removed and the amount of polymer in the solution is determined. The same procedure is performed using 2,6-dinitro-4-sec-butyl phenol (24DNBP) instead of 2,4-dinitro-4-sec-butyl phenol. Finally, the same procedure is performed using a 50/50 mixture of 2,4-dinitro-4-sec-butyl phenol and 2,6-dinitro-4-sec-butyl phenol (50/50 Mixture) instead of 2,4-dinitro-4-sec-butyl phenol. The results set forth in the Table I indicate that there is essentially no experimental difference between 2,4-dinitro-4-sec-butyl phenol, 2,6-dinitro-4-sec-butyl phenol and the 50/50 mixture.

TABLE II

Styrene Polymerization Inhibition Data

| Hours | 24DNBP | 26DNBP | 50/50 Mixture |
|---|---|---|---|
| 0.5 | 0.35 | 0.23 | 0.29 |
| 1.0 | 0.67 | 0.64 | 0.48 |
| 1.5 | 1.10 | 0.78 | 0.93 |
| 2.0 | 1.47 | 1.38 | 1.19 |
| 3.0 | 2.65 | 2.15 | 1.87 |
| 4.0 | 4.97 | 3.47 | 3.95 |

Thus, a mixture of at least one compound of formula (I) and at least one compound of formula (II) is as an effective polymerization inhibitor as the pure 24DNBP which is the current polymerization inhibitor in general use today. Moreover, because a mixture is as effective an inhibitor, the manufacturing process can be greatly simplified resulting in significant cost savings and throughput enhancements.

All references cited herein are incorporated by reference. Although the invention has been disclosed with reference to its preferred embodiments, from reading this description those of skill in the art may appreciate changes and modifications that may be made which do not depart from the scope and spirit of the invention as described above and claimed hereafter.

What is claimed is:

1. A polymerization inhibiting composition comprising a neat combination of a compound of formula (I)

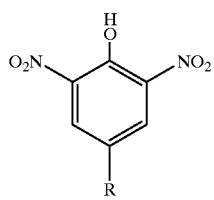
(I)

and a compound of formula (II)

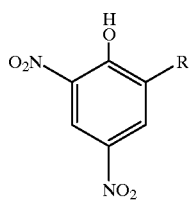
(II)

where R is an alkyl group having between about 3 and about 12 carbon atoms.

2. The composition of claim 1, wherein the R is an alkyl group having between 4 and 6 carbon atoms.

3. The composition of claim 1, wherein the R is an alkyl group having between 4 and 5 carbon atoms.

4. The composition of claim 1, wherein the R is a sec-butyl group.

5. The composition of claim 1, where the combination comprises about 5 wt % to about 95 wt. % of the compound of formula (I) to about 95 wt. % to about 5 wt % of the compound of formula (II).

6. A composition comprising a vinyl monomer and an effective amount of a inhibitor composition comprising a compound of formula (I)

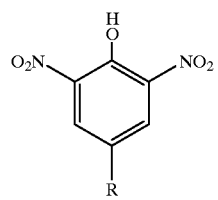
(I)

and a compound of formula (I)

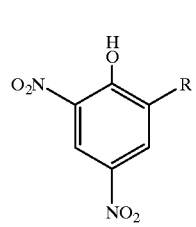
(II)

where R is an alkyl group having between about 3 and about 12 carbon atoms.

7. The composition of claim 6, further comprising a solvent.

8. The composition of claim 6, wherein the solvent is an aromatic solvent.

9. The composition of claim 6, wherein the R is an alkyl group having between 4 and 6 carbon atoms.

10. The composition of claim 6, wherein the R is an alkyl group having between 4 and 5 carbon atoms.

11. The composition of claim 6, wherein the R is a sec-butyl group.

12. The composition of claim 6, where the combination comprises about 5 wt % to about 95 wt. % of the compound of formula (I) to about 95 wt. % to about 5 wt % of the compound of formula (II).

13. A method for preparing a polymerization inhibitor comprising the steps of:
   contacting a hydroxy aromatic compound with a C3 to C12 olefin under alkylation conditions to form an alkylated hydroxy aromatic intermediate product; and
   contacting the alkylated hydroxy aromatic intermediate product with a nitrating agent comprising nitric acid in the absence of oxygen under conditions sufficient to promote dinitration of all mono-alkylated hydroxy aromatic compounds in the intermediate product.

14. The method of claim 13, further comprising the step of:
   separating all monoalkylated hydroxy aromatic compounds from higher alkylated hydroxy aromatic compounds.

15. The method of claim 13, wherein the first contacting step comprises:
   alkylating an amount of the hydroxy aromatic compound with the alkene where the amount of hydroxy aromatic compound is greater than a stoichiometric amount of hydroxy aromatic compound to alkene;
   separating an unreacted hydroxy aromatic compound from the intermediate product; and
   recycling the unreacted hydroxy aromatic compound to the contacting step.

16. A process of inhibiting polymerization comprising the step of:

adding an effective amount of a composition comprising a combination of a compound of formula (I)

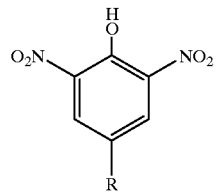
(I)

and a compound of formula (II)

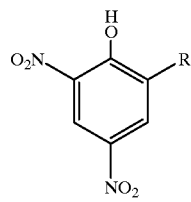
(II)

where R is an alkyl group having between about 3 and about 12 carbon atoms to a vinyl monomer composition, where the effective amount inhibits vinyl monomer polymerization.

17. The process of claim 16, wherein the R is an alkyl group having between 4 and 6 carbon atoms.

18. The process of claim 16, wherein the R is an alkyl group having between 4 and 5 carbon atoms.

19. The process of claim 16, wherein the R is a sec-butyl group.

20. The process of claim 16, where the combination comprises about 5 wt % to about 95 wt. % of the compound of formula (I) to about 5 wt. % to about 95 wt % of the compound of formula (II).

* * * * *